United States Patent [19]
Eibl et al.

[11] Patent Number: 5,675,058
[45] Date of Patent: Oct. 7, 1997

[54] BIOASSAY FOR THROMBOGENESIS AND RABBIT MODEL

[75] Inventors: Johann J. Eibl; Hans P. Schwarz; Ludwig Pichler, all of Vienna, Austria

[73] Assignee: Immuno AG, Vienna, Austria

[21] Appl. No.: 116,845

[22] Filed: Sep. 7, 1993

Related U.S. Application Data

[63] Continuation of Ser. No. 834,066, Feb. 11, 1992, abandoned.
[51] Int. Cl.$^6$ .................... C12N 5/00; A61K 51/00; G01N 33/48
[52] U.S. Cl. ................... 800/2; 800/DIG. 5; 424/9; 435/13
[58] Field of Search ........................ 424/9; 800/2

[56] References Cited

PUBLICATIONS

Wessler et al (1959) J. Applied Physio. 14, 943–946.
Jones et al (1974) Infection and Immunity 10, 1343–1349.
Cybulsky et al (1988) Lab. Invest. 58, 365–378.
Fareed et al. *Seminars in Thrombosis and Hemostasis* 11(2): 155–75 (1985).
Galanos et al. *PNAS* U.S.A. 76 (11): 5939–43 (1979).

Primary Examiner—Jacqueline M. Stone
Assistant Examiner—Deborah Crouch
Attorney, Agent, or Firm—Foley & Lardner

[57] ABSTRACT

An in vivo assay for determining the potential thrombogenic activity of a test compound entails pre-treating an animal with both a hepatoxin and either a bacterial agent (whole bacteria or bacterial toxins, including endotoxins) or a bacterial agent-induced cytokine, which pre-treatment enhances sensitivity to thrombogenic substances. The sensitized animal can be used in identifying a thrombogenic substance even when it is a weak potentiator of thrombogenesis, and in detecting smaller amounts of a strong potentiator.

14 Claims, 1 Drawing Sheet

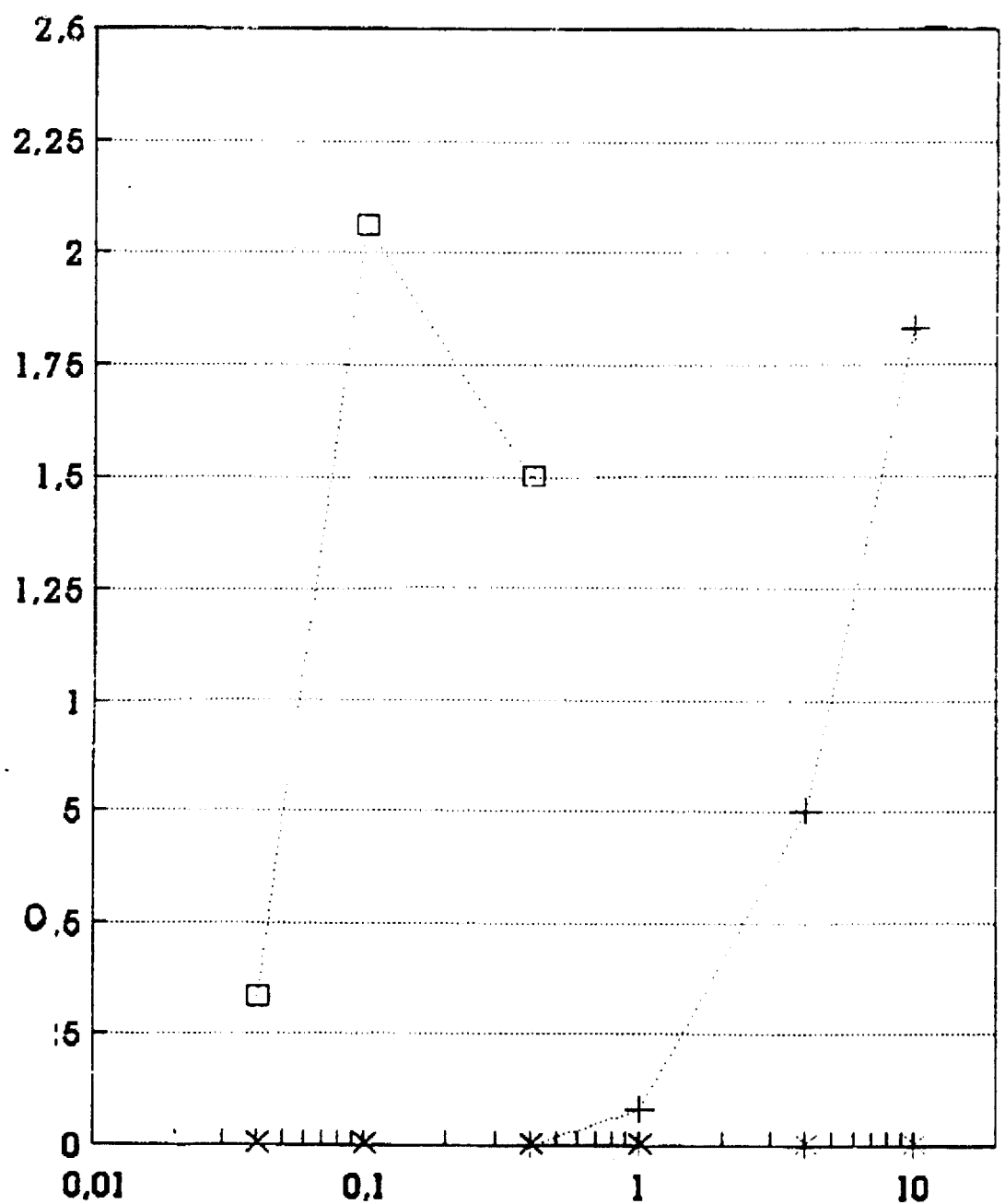

BIOASSAY FOR THROMBOGENESIS AND RABBIT MODEL

This is a continuation of application Ser. No. 07/834,066, filed Feb. 11, 1992, now abandoned.

BACKGROUND OF THE INVENTION

The present invention relates both to a bioassay method and to an animal model for determining the potential thrombogenic activity of a test compound. The bioassay is characterized by pre-treating an animal with a hepatoxin and a bacterial agent or bacterial agent-induced cytokine to enhance the sensitivity of an animal upon exposure to thrombogenic substances. The bioassay method, as well as the animal model, detects minute thrombosis-inducing activity of a compound.

A pharmaceutical compound, or an agent or factor isolated from mammalian blood may be successfully administered to patients suffering from various diseases associated with impaired blood coagulation. But infusing patients with such an agent or compound may induce a hypercoagulable state where such compound, agent or factor possesses intrinsic coagulation enhancing properties and or is contaminated with any procoagulent factor which makes it potentially thrombogenic.

The undesirable side effects of such a compound or agent may include thrombophlebitis, deep vein thrombosis, arterial conclusion and consumptive coagulopathies. In the extreme, a coronary thrombosis may develop and the resulting occlusion of a coronary artery can cause sudden death or a myocardial infarction. More commonly, a phlebitis condition may develop causing the patient to suffer from edema, stiffness, severe pain and perhaps even dangerous septicemia.

It is crucial to evaluate the thrombogenic potential of a pharmaceutical compound, or of an agent isolated from blood to be administered to a patient, especially because many patients maintain an enhanced susceptibility towards coagulation due disease, illness or genetic abnormality. In particular, patients having impaired liver function (hepatosis) and/or an acute or chronic infection may be predisposed to hypercoagulation.

An impaired liver function leads to a reduction in the synthesis of antithrombotic proteins such as protein C, protein S and antithrombin III. Further, the elimination by means of clearance through the liver of activated factors or coagulative fragments may be retarded. Thus, the hemostatic system is thrown off balance and a latent hypercoagulable state is induced.

In addition to hepatosis, a variety of opportunistic infections may induce a hypercoagulable state in the patient which may lead to thrombosis. This is attributed at least in part to the activity of cytokines.

Blood product agents, such as proteins isolated from serum, in the past were tested for thrombogenic action by using a stasis animal model. The Wessler stasis thrombosis model, see Wessler et al., *J. Appl. Physiol.* 14:943–46 (1959), was widely used for the evaluation of the thrombogenic action of numerous agents. Essentially, the Wessler model provides a bioassay wherein an animal is anesthetized, and a small section of jugular vein surgically isolated. Next, upon infusion of a test sample to be investigated for its thrombogenic properties, the previously freed segment of jugular vein is promptly occluded with clamps. The vein segment remains in situ for 10 minutes. The segment is then removed from the animal and its contents emptied for detection of clot formation. Evidence that the test sample accelerates coagulation within the isolated segment can be found by examining the amount of the clot formed under the stasis conditions. The clot size is scored on a scale from 0 to 4, and a comparative value of a test sample's thrombogenicity thus is obtained.

A drawback to the Wessler stasis bioassay is that, in order to elicit thrombogenicity, large doses of test substances must be infused. Attempts have been made to develop a more sensitive stasis model for testing thrombogenicity of various agents, see Fareed et al., *Seminars in Thrombosis and Hemostasis* 11:155–75 (1985). Fareed injects Russel's viper venom immediately following the injection of a test compound into a stasis animal model. The injected viper venom activates blood serum factor X and elevates factor Xa levels, which increases coagulation potential. Factor X is one of more than a dozen proteins which interact together in a cascading series to achieve the formation of fibrin and subsequent coagulation of blood.

SUMMARY OF THE INVENTION

It is therefore an object of the present invention to provide a bioassay for thrombogenicity which is highly sensitive and, hence, does not require large amounts of test compound.

It is a further object of the present invention to provide a methodology for detecting even a weakly thrombogenic substance in situ.

It is yet another object of the present invention to provide an animal model which is readily implementable and is useful in assessing the thrombogenic activity of a wide range of compounds.

It is still another object of the present invention to provide a kit for detecting thrombogenic activity, which kit is employed in preparing the aforementioned animal model.

In accomplishing the foregoing objects, there has been provided, in accordance with one aspect of the present invention an in vivo assay for detection of thrombogenic activity of a compound, comprising the steps of (A) introducing into an animal (i) a first compound that is a hepatoxin and (ii) a second compound that is a bacterial agent or bacterial agent-induced cytokine; (B) introducing a test compound systemically into the animal; then (C) restricting flow through a circulatory vessel in an animal such that a volume of blood is isolated within a delimited portion of the vessel; and thereafter (D) determining the extent of thrombogenesis within the portion of the vessel. In one preferred embodiment, step (A) comprises introducing the first compound and the second compound separately into the animal, while in another preferred embodiment the first compound is introduced prior to introducing the second compound into the animal.

There has also been provided, in accordance with another aspect of the present invention, an animal model for detecting thrombogenic activity of a compound, comprising an animal that contains a hepatoxin and a bacterial agent or bacterial agent-induced cytokine in sufficient amounts, respectively, to increase susceptibility of said animal to a thrombogenic substance, wherein flow through a circulatory vessel of the animal has been restricted such that a volume of blood is isolated within a delimited portion of the vessel.

In accordance with yet another aspect of the present invention, a kit has been provided for detection of thrombogenic activity of a compound, comprising a first receptacle containing a hepatoxin and a second receptacle containing a bacterial agent or a bacterial agent-induced cytokine, wherein said first and second receptacle are ampules. In a preferred embodiment, the kit further comprises a receptacle containing labelled thrombophilic substance.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

FIG. 1 is a line-drawing of a graph which depicts the relationship between dose of activated prothrombin complex, a test agent isolated from blood, and thrombogenic activity measured via an animal model of the present invention. The ordinate shows mean scored values in relation to a standard set of thrombi sizes; the abscissa shows dosage (logarithmic scale). Squares (■) denote data points obtained upon introduction of the test agent in accordance with Example I, while plus marks (+) denote comparative data obtained by employing the test agent to untreated animals (Wessler model) as in Example II.

DETAILED DESCRIPTION OF PREFERRED EMBODIMENTS

The present invention provides a sensitive tool for evaluating the potential thrombogenicity of a compound or an agent isolated from blood, such as a serum protein. It has been discovered that introduction into an animal of a hepatoxin and a particular type of bacterial agent (or a cytokine induced thereby), prior to injection of a test sample, sensitizes the animal to thrombogenic activity and, hence, makes possible a more sensitive bioassay for identifying substances that induce clot formation (thrombogenesis).

The sensitivity of the animal model and bioassay of the present invention permits detection of thrombogenic activity using lesser amounts of a test compound, which conserves the test compound for further research. Also, because of the increased sensitivity of the bioassay of the invention, thrombogenic activity is now be detected which was previously undetectable. The invention includes a kit containing the components hepatoxin and a bacterial agent or bacterial agent-induced cytokine to facilitate employment of the assay. According to the present invention a hepatoxic agent is used in combination with a bacterial agent to enhance an animal's susceptibility toward clot formation. It has been discovered that introduction of these agents activates the coagulopathic response in animals. Upon the administration of minimal amounts of thrombogenic substances to an animal sensitized in accordance with the invention, a quantifiable amount of thrombi are generated in this stasis model.

It is useful to evaluate, by means of an animal model within the invention, the potential thrombogenicity of a substance, including a compound suspected of having coagulant-modulating activity, as well a blood product (serum protein). For example, a blood coagulation factor concentrate such as factor VIIa, prothrombin complex or activated prothrombin complex, or an immunoglobulin can be sensitively assayed using the model of the present invention.

A bioassay within the present invention can be used to test a compound, such as factor VIIa or factor VIII, which has been produced by recombinant means. Illustrative of recombinantly-produced compounds in this regard are any protein from a group of recombinantly-produced, activated blood products and muteins thereof which display thrombosis-inducing activity, where a "mutein" is a protein with an amino-acid sequence having a deletion, substitution or insertion in relation to a natural counterpart. Additionally, certain synthetic compounds, such as synthetic phospholipids, which are known to have coagulant-modulating activity are also candidate test compounds. In this regard, a negative result obtained using the present assay method permits a reliable evaluation of a blood product or compound as being non-thrombogenic.

The choice of mammalian laboratory animal to use in accordance with the present invention is not critical so long as a vessel of the chosen species is accessible surgically to the manipulations required for the bioassay. In this context any circulatory vessel having diameter between about 3–6 millimeters and length of about 1–2 centimeters should be usable. Thus, a rabbit is preferred due to the relative ease of surgically exposing the jugular vein, and for economic efficiency. Illustrative of other suitable test animals are dog, cat, rat, goat, pig, chicken, cow, horse and monkey.

The method of the present invention provides for a pretreatment regimen including the step of administering a hepatoxin and bacterial agent to the animal prior to the introduction of the test compound. A "hepatoxin" as used in the context of the invention, is defined as any of a class of agents having a toxic effect on hepatocytes, and producing a coagulant-modulating effect in an animal model when utilized in conjunction with bacterial agent or cytokine in the regimen described below.

Representative of hepatoxic agents which are useful in the present invention are galactosamine, lead acetate, α-amanitin, carbon tetrachloride and polychlorodibenzo-dioxins. Preferred hepatoxins include galactosamine (2-amino-2-deoxy-D-galactose), a widely distributed polysaccharide, and 2,3,7,8-tetra-chlorodibenzo-p-dioxin.

In this context, the term "bacterial agent" denotes any from a group of agents characterized by an ability to increase the coagulation potential of the animal, including: live or killed gram-negative and gram-positive bacteria, or components thereof, or "bacterial toxin", as defined below.

Illustrative of gram-negative bacteria for use in the model are species of the genera Salmonella, Escherichia, Serratia and Neisseria, preferably *Salmonella typhimurium* or *Neisseria meningitides*. Examples of gram-positive bacteria include Staphylococcus and Mycobacterium, preferably *S. aureus* or *M. tuberculosis*. Live bacteria are useful in the invention, as are killed bacteria, or bacterial components obtained by conventional methods. For example, killed bacteria or bacterial components are obtained by heat treating or extraction, respectively.

In addition to bacteria itself, "bacterial toxin, " particularly endotoxic components extracted from bacterial cell walls, such as lipopolysaccharide (LPS) from gram-negative bacteria, is effective in the animal model. The gram-positive amphipathic equivalent of LPS, lipoteichoic acid, is effective as well.

A "bacterial agent-induced cytokine" is defined in this context as any from a group of cytokines characterized by an ability to increase the coagulation potential of the animal when introduced in conjunction with a hepatoxin according to the present invention. Illustrative of cytokines useful in the model include IL-1, IL-2, IL-3, IL-4, IL-5 and IL-6, tumor necrosis factor, transforming growth factor β, and an interferon.

A bacterial agent or bacterial agent-induced cytokine as described above is effective in the animal model of the invention provided that upon application into an animal together with a hepatoxin as taught by the invention, the coagulation potential of an animal is increased. To determine whether the bacterial agent or cytokine is effective in the invention, a variation of the model described in the invention is employed.

The varied procedure employed to test efficacy of a bacterial agent or bacterial agent-induced cytokine includes a first step of introducing into an animal a hepatoxin of known efficacy according to the invention. This is followed by introducing an "uncharacterized" bacterial agent or cytokine, followed by introduction of a known thrombogenic agent (as opposed to a test compound). The effectiveness of the uncharacterized bacterial agent or bacterial agent-induced cytokine is determined by comparison of a thrombogenicity value obtained where the uncharacterized agent was used, versus a thrombogenicity value obtained where a known effective bacterial agent or cytokine was employed in conjunction with the same hepatoxin and thrombogenic agent used as employed in connection with the "uncharacterized" agent. An effective bacterial agent or bacterial agent-induced cytokine is identified where a thrombogenicity value is obtained that is comparable to a thrombogenicity value obtained using a known effective bacterial agent or bacterial agent-induced cytokine in conjunction with the same hepatoxin and thrombogenic agent in accordance with the invention.

Likewise, to determine whether a particular hepatoxin is effective in the context of the model system of the invention, upon application into an animal together with an effective bacterial agent or bacterial agent-induced cytokine in a manner according to the invention, the coagulation potential of an animal is increased. A determination as to whether a hepatoxin is effective in the invention is made by introducing it into a test animal, followed by introduction of a bacterial agent or cytokine which has known efficacy in the bioassay of the invention, and further followed by application of compound having known thrombogenicity. The effectiveness of the uncharacterized hepatoxic agent is determined by comparison of a thrombogenicity value obtained where the uncharacterized agent was used, versus a thrombogenicity value obtained where a known effective hepatoxic agent was employed in conjunction with the same bacterial agent or bacterial agent-induced cytokine and known thrombogenic agent used as employed in connection with the "uncharacterized" agent. An effective hepatoxin is identified where a thrombogenicity value is obtained that is comparable to a thrombogenicity value obtained using the same effective bacterial agent or bacterial agent-induced cytokine in conjunction with an effective hepatoxin and same thrombogenic agent in accordance with the method of the invention.

The pretreatment regimen according to the invention which enhances the thrombogenicity of a test animal includes systemic administration of a hepatoxic agent and a bacterial agent or bacterial agent-induced cytokine to a test animal either as a mixture or separately. Preferably, hepatoxin is introduced prior to bacterial agent, and in a more preferred embodiment, the interval of time passing between introduction of hepatoxin and bacterial agent is about 3.5 hours. The hepatoxin can be introduced at time between thirty minutes to six hours before the introduction of the test compound, while bacterial agent or cytokine is introduced either simultaneously with hepatoxin, or at some point after the introduction of hepatoxin no longer than about six hours prior to the introduction of said test compound into said animal. More preferably, the hepatoxin is introduced at time about three to five hours before the introduction of the test compound, while bacterial agent is introduced about one to two hours prior to the introduction of test compound.

According to the pretreatment regimen of the invention, a hepatoxic agent is introduced systemically at concentration between 100–1000 mg/kg, and a bacterial agent or cytokine introduced systemically (generally, after an interval of time has lapsed in accordance with the temporal guidelines above), at a concentration between 10–500 µg/kg to a test animal. In a preferred embodiment, hepatoxin such as galactosamine is introduced at a concentration of about 350 mg/kg, while a bacterial agent, such as endotoxin of S. typhimurium, is introduced at a concentration of about 100 µg/kg.

An animal treated with hepatoxin and endotoxin as described above is narcotized in a conventional manner, such as by systemic administration of a sufficient amount of anesthesia. In a preferred embodiment, phenobarbital natrium is administered in an amount between 30–42.5 mg/kg after the administration of endotoxin. The interval of time between endotoxin and narcotization is not critical. The animal is given a local anaesthetic at the site identified for vascular surgery.

Upon anesthetization of the animal, surgery is performed to isolate a vessel for experimentation. Preferably the collateral vessels are ligated, clamped, or otherwise occluded. A test compound or blood product agent is administered systemically, in an amount sufficient to characterize its thrombogenicity, and being administered with a pharmaceutically acceptable carrier. The amount varies depending upon the nature of the compound. A useful range for prothrombin complex, for example, includes about 0.01–10 U/kg. Because of the sensitivity of this model system, many test compounds will be administrable in quantities of less than 10 U/kg, and in some instances, less than 4 U/kg.

Blood flow to the isolated blood vessel of the test animal is interrupted in the delimited portion of the vessel by clamping, ligating or otherwise fully occluding the vessel. The restricted vessel remains in situ for a period of ten minutes before being removed from the animal for examination of thrombi produced.

The generated thrombi can be examined by removing the vessel and placing it in a Petri dish or other location suitable for display of vessel contents. Thrombi can be quantified by several methods, such as by comparing said clot against a set of generated standard clot sizes, or by determining extent of the clot densitometrically, or by detecting a labelled thrombophilic substance (which was introduced into the animal prior to administration of the test compound) and correlating the amount of incorporated label to the extent of clot formation.

To utilize a labelled thrombophilic substance to evaluate the extent of clot formation in the bioassay of the invention requires an additional step of introducing the labelled thrombophilic substance prior to the introduction of test compound. The time of addition of labelled thrombophilic substance is not critical, so long as it is present in an adequate concentration during thrombogenesis. Any protein that is both incorporated into the thrombi and can be labelled, can be used to detect the extent of thrombogenesis in accordance with the present invention. Radioactively labelled fibrinogen ($^{125}$fibrinogen), which is incorporated in a thrombus by formation of $^{125}$fibrin, is an example of a labelled protein useful in the present invention.

To facilitate employment of the bioassay, a kit is provided according to the invention which includes a receptacle containing a solution of hepatoxin in a pharmaceutically acceptable carrier, or in lyophilized form. Preferably the hepatoxin solution is in a pharmacologically effective concentration for purposes of the bioassay. The kit also includes a receptacle containing a solution of bacterial agent or bacterial agent-induced cytokine in a pharmaceutically acceptable carrier, or in lyophilized form. Preferably bacterial agent or bacterial agent-induced cytokine are present in a pharmacologically effective concentration for purposes of the bioassay. A receptacle useful for purposes of the kit can be an ampule, a syringe or vial and is preferably packaged under sterile conditions.

A kit according to the invention includes a labelled thrombophilic substance (to be utilized in detection of thrombi) or an unlabelled thrombophilic substance which may be labelled in a conventional manner prior to its introduction into the animal in the context of the bioassay. A preferred label in this context is a radioactive element, however, other labels which have properties suitable to allow detection upon incorporation of the label within the clot can be utilized.

The present invention is further described with reference to the following, illustrative examples.

EXAMPLE 1

EVALUATION AN ACTIVATED PROTHROMBIN COMPLEX PREPARATION FOR THROMBOGENICITY

Rabbits were treated with 350 mg/kg galactosamine intraperitoneally. Each animal received 0.1 mg/kg endotoxin of S. typhimurium intraperitoneally 3.5 hours later. Treatment of the rabbits with either of the agents alone remained without thrombogenic effect (score X-0.1, n-8).

Rabbits treated as described in the foregoing paragraph were narcotized (pentobarbital natrium, 30–42.5 mg/kg intravenously into an ear vein) an hour after the administration of the endotoxin. After additional anesthesia with procaine HCl in the neck, a portion of the vena jugularis 1–2 cm in length was freed from its surrounding structures and its collaterals were ligated. The activated prothrombin complex preparation was introduced in dosages of 0.04, 0.1 and 0.4 U/kg to each of 6 animals in the following manner.

After reconstitution in water for injection and dilution in isotonic saline solution, the activated prothrombin complex preparation was injected within 15 seconds into a contralateral rabbit ear vein. After 25 seconds, the ligatures were tightened, the previously exposed jugular vein then remained in place for 10 minutes before being removed from the animal. The ligated vessel was then removed and placed in a Petri dish, opened and examined for clot formation.

Thrombi are evaluated using the following score-system:

| Generation of Thrombi | Score |
| --- | --- |
| liquid blood without thrombi | 0 |
| some small thrombi | 0.5–1 |
| some medium or many small thrombi | 2 |
| a large amount of medium thrombi | 3 |
| some larger thrombi | 3.5 |
| a single large thrombus | 4 |

The size of the clot was scored as described above. FIG. 1 shows the dose of activated prothrombin complex preparation which produces a score of 1 or, equivalently, ED1.

EXAMPLE 2

A COMPARISON OF THE BIOASSAY OF THE INVENTION WITH THE WESSLER MODEL

For purposes of comparison to the described model, the activated prothrombin complex preparation was introduced in dosages of 0.4, 1, 4 and 10 U/kg in untreated (naive) animals according to the Wessler model. The dose which produces a score of 1 is defined as the ED1. Using the Wessler model (no endotoxin/galactosamine pretreatment), the ED1 is 5 U/kg, whereas with the model according to the invention, the ED1 is 0.06 U/kg. Thus, the bioassay of the invention increases sensitivity by approximately by a factor of 83.

EXAMPLE 3

ASSAY OF FACTOR IX COMPLEX

A preparation of factor IX complex (Bebulin IMMUNO, 200 U/kg) was infused intravenously into six animals obtained and treated as described in Example I.

No thrombus could be detected with the Wessler model, whereas a score of 1.7 was determined using the model according to the invention.

What is claimed is:

1. An in vivo stasis assay method for detection of thrombogenic activity of a composition, comprising the steps of (A) injecting into a rabbit (i) a first compound that is a hepatoxin and (ii) a second compound that is an endotoxin, wherein said first compound and said second compound sensitize said animal to thrombogenesis without causing thrombogenesis; (B) injecting said composition into said rabbit; then (C) restricting flow through a circulatory vessel in said rabbit such that a volume of blood is isolated within a delimited portion of said vessel; and thereafter (D) determining the extent of thrombogenesis within said delimited portion of said vessel based upon an evaluation of visible thrombi.

2. An in vivo stasis assay method according to claim 1, wherein step (A) comprises injecting said first compound and said second compound separately into said rabbit.

3. An in vivo stasis assay method according to claim 2, wherein step (A) comprises introducing said first compound prior to introducing said second compound into said rabbit.

4. An in vivo stasis assay method according to claim 1, wherein said first compound is injected at time between 0.5 and 6 hours prior to the injection of said composition, and said second compound is injected between 0 and 5.5 hours prior to the injection of said composition into said rabbit.

5. An in vivo stasis assay method according to claim 4, wherein said first compound is injected about 3.5 hours prior to said injection of said second compound.

6. An in vivo stasis assay method according to claim 5, wherein said first compound is galactosamine and is injected into said rabbit at a concentration between 100 to 1000 mg/kg.

7. An in vivo stasis assay method according to claim 6, wherein said galactosamine is injected at a concentration between 300 to 400 mg/kg.

8. An in vivo stasis assay method according to claim 1, wherein said hepatoxin is injected at a concentration between 100 to 1000 mg/kg.

9. An in vivo stasis assay method according to claim 1, wherein said endotoxin is introduced at a concentration between 10 to 500 µg/kg.

10. An in vivo stasis assay method according to claim 1, wherein step (A) further comprises the step of injecting into rabbit a labeled thrombophilic substance, and step (D) further comprises isolating visible thrombi from said delimited portion of said vessel and determining the amount of incorporated label from said labeled thrombophilic substance.

11. An in vivo stasis assay method according to claim 1, wherein step (D) further comprises isolating visible thrombi from said delimited portion of said vessel and weighing said thrombi.

12. An in vivo assay method according to claim 1, wherein step (D) further comprises isolating visible thrombi from said delimited portion of said vessel and determining thrombi size densitometrically.

13. A stasis rabbit model for detecting thrombogenic activity of a compound, comprising a rabbit that has been injected with effective amounts of a hepatoxin and an endotoxin to increase susceptibility of said rabbit to thrombogenesis without causing thrombogenesis.

14. A kit for in vivo detection of thrombogenic activity of a compound by a stasis rabbit model, comprising a first receptacle containing a hepatoxin, a second receptacle containing an endotoxin and a third receptacle containing a labeled thrombophilic substance, wherein said hepatoxin, said endotoxin and said thrombophilic substance can be injected into a rabbit to increase the susceptibility of said rabbit to thrombogenesis without causing thrombogenesis.

* * * * *